(12) United States Patent
Kozono et al.

(10) Patent No.: US 10,668,091 B2
(45) Date of Patent: Jun. 2, 2020

(54) ANTIBACTERIAL AGENT AGAINST MULTIDRUG-RESISTANT GRAM-POSITIVE BACTERIA AND EXTERNAL AGENT

(71) Applicant: KEWPIE CORPORATION, Tokyo (JP)

(72) Inventors: Marie Kozono, Tokyo (JP); Hideto Yoshida, Tokyo (JP)

(73) Assignee: KEWPIE CORPORATION, Tokyo (JP)

( * ) Notice: Subject to any disclaimer, the term of this patent is extended or adjusted under 35 U.S.C. 154(b) by 0 days.

(21) Appl. No.: 16/006,443

(22) Filed: Jun. 12, 2018

(65) Prior Publication Data

US 2018/0289726 A1 Oct. 11, 2018

Related U.S. Application Data

(63) Continuation of application No. 15/100,521, filed as application No. PCT/JP2013/082040 on Nov. 28, 2013, now abandoned.

(51) Int. Cl.

| | | |
|---|---|---|
| A61K 31/685 | (2006.01) | |
| A61K 31/683 | (2006.01) | |
| A61K 31/7024 | (2006.01) | |
| A61K 47/10 | (2017.01) | |
| A61K 47/12 | (2006.01) | |
| A61K 47/14 | (2017.01) | |
| A61K 9/00 | (2006.01) | |
| A61K 9/06 | (2006.01) | |
| A61K 9/08 | (2006.01) | |
| A61K 47/16 | (2006.01) | |
| A61K 47/18 | (2017.01) | |
| A61K 47/24 | (2006.01) | |
| A61K 47/44 | (2017.01) | |
| A61K 9/12 | (2006.01) | |

(52) U.S. Cl.
CPC .......... *A61K 31/685* (2013.01); *A61K 9/0014* (2013.01); *A61K 9/06* (2013.01); *A61K 9/08* (2013.01); *A61K 9/12* (2013.01); *A61K 31/683* (2013.01); *A61K 31/7024* (2013.01); *A61K 47/10* (2013.01); *A61K 47/12* (2013.01); *A61K 47/14* (2013.01); *A61K 47/16* (2013.01); *A61K 47/183* (2013.01); *A61K 47/24* (2013.01); *A61K 47/44* (2013.01)

(58) Field of Classification Search
CPC .... A61K 31/685; A61K 31/7024; A61K 9/12; A61K 31/683; A61K 47/44; A61K 9/08; A61K 9/06; A61K 47/24; A61K 47/183; A61K 47/16; A61K 47/14; A61K 47/12; A61K 47/10; A61K 9/0014
USPC ....................................................... 514/2.4
See application file for complete search history.

(56) References Cited

U.S. PATENT DOCUMENTS 5,716,814 A 2/1998 Yesair
2009/0281065 A1* 11/2009 Ramchand .......... A61K 31/662
514/114

FOREIGN PATENT DOCUMENTS

| | | |
|---|---|---|
| JP | 05-011937 A | 1/1993 |
| JP | 2001-523723 A | 11/2001 |
| JP | 2003-089660 A | 3/2003 |
| JP | 2011-256160 A | 12/2011 |
| JP | 2015-101580 A | 6/2015 |

OTHER PUBLICATIONS

Tsuchido T. Induction of cell autolysis of Bacillus subtilis with lysophosphatidylcholine. Appl Microbiol Biotechnol (1994) 41:106-109. (Year: 1994).*
Hugo et al. The Role of Cellular Lipid in the Resistance of Gram-positive Bacteria to Penicillins. Micorbiology (1966), 42, 133-138. (Year: 1966).*
Joshi et al. Modification of lecithin by physical, chemical and enzymatic methods. Eur. J. Lipid Sci. Technol. 108 (2006) 363-373. (Year: 2006).*
International Search Report in International Application No. PCT/JP2013/082040, filed Nov. 28, 2013.
Takahashi, T., "Lytic Susceptibility of Staphylococcal L-Forms to Lysolecithin," *Microbiology and Immunology*, 1980, 24(5):463-468.
Kondo, E. et al., "Mechanism of Bactericidal Activity of Lysolecithin and Its Biological Implication," *Japanese Journal of Medical Science & Biology*, 1985, 38:181-194.
Furukawa, S. et al., "Sugar fatty acid esters inhibit biofilm formation by food-borne pathogenic bacteria," *International Journal of Food Microbiology*, 2010, 138:176-180, Elsevier B.V.
Miyamoto, T. et al., "Inhibition of Adhesion of Several Bacteria onto Microtiter Plate by Selected Food Additives," *Japanese Journal of Food Microbiology*, 2011, 28(3):157-166.
Lahav, M. et al., "Effect of leukocyte hydrolases on bacteria. XIII. Role played by leukocyte extracts, lysolecithin, phospholipase a2, lysozyme, cationic proteins, and detergents in the solubilization of lipids from Staphylococcus aureus and group A streptococci: relation to bactericidal and bacteriolytic reactions in inflammatory sites," *Inflammation*, Sep. 1979, 3(4):365-377.
Murata, T. "Attempt at the eradication on MRSA infectious disease," *Rinsho to Kenkyu*, 1992, 69(8):130-134.

(Continued)

*Primary Examiner* — Yih-Horng Shiao
(74) *Attorney, Agent, or Firm* — Saliwanchik, Lloyd & Eisenschenk (57) ABSTRACT

To provide a multidrug-resistant Gram positive bacteria antibacterial agent containing as an active ingredient a novel component to which multidrug-resistant bacteria are not resistant, and an external agent containing the same. The multidrug resistant Gram-positive bacteria antibacterial agent according to the present invention contains an amphipathic compound having an HLB value of greater than 9.5 and 20 or less and an acyl group as an active ingredient. The external agent according to the present invention contains the multidrug resistant Gram-positive bacteria antibacterial agent.

20 Claims, 1 Drawing Sheet

(56) References Cited

OTHER PUBLICATIONS

Nobmann, P. et al., "In vitro antimicrobial activity and mechanism of action of novel carbohydrate fatty acid derivatives against *Staphylococcus aureus* and MRSA," *Journal of Applied Microbiology*, 2010, 108(6):2152-2161, 2009 The Society for Applied Microbiology.
Coonrod, J.D. et al., "Detection and Partial Characterization of Antibacterial Factor(s) in Alveolar Lining Material of Rats," *The Journal of Clinical Investigation*, Jan. 1983, 71(1):129-141.
Partial Supplementary European Search Report dated Jun. 9, 2017 in European Application No. 13898285.5.
Peterson, J.K. et al., "Isolation and Structural Identification of Sucrose Esters From Corn Spurrey (*Spergula arvensis*); Inhibition of Seed Germination," *Journal of Chemical Ecology*, 1998, 24(11):1803-259, Plenum Publishing Corporation.
Saunders, L. et al., "Detection of Lysolecithin in a Sample of Egg Lecithin," *Journal of Pharmacy and Pharmacology*, Dec. 1960, 12(Suppl):257-259.
Office Action dated Jan. 24, 2018 in Japanese Application No. 2015-550266, along with its English translation.
Fragrance Journal, 2000, 28(12):58-64.
Food Hygiene Journal, 1987, 28(4):261-266.

\* cited by examiner

ANTIBACTERIAL AGENT AGAINST MULTIDRUG-RESISTANT GRAM-POSITIVE BACTERIA AND EXTERNAL AGENT

CROSS-REFERENCE TO RELATED APPLICATIONS

This application is a continuation of U.S. application Ser. No. 15/100,521, filed May 31, 2016, which is the U.S. national stage application of International Patent Application No. PCT/JP2013/082040, filed Nov. 28, 2013, the disclosures of which are incorporated herein by reference in their entirety.

TECHNICAL FIELD

The present invention relates to an antibacterial agent against multidrug-resistant Gram-positive bacteria, and an external agent containing the same.

BACKGROUND ART

Multidrug resistant bacteria resistant to a number of medical agents raise an issue. In particular, methicillin-resistant Staphylococcus aureus (MRSA) among the multidrug resistant bacteria is Staphylococcus aureus resistant to methicillin that is an antibiotic, and may be resistant to a plurality of antibiotics including methicillin. MRSA infections often are seen in nosocomial infections. As there may be serious infectious cases, sufficient countermeasures are required.

As the countermeasures for multidrug resistant bacterial infections, it is considered to use an antibiotic that does not acquire resistance. However, the use of antibiotics generates a new resistant bacteria, and there is a possibility that countermeasures become more difficult.

Meanwhile, there is a substance other than antibiotics having antibacterial properties against Gram-positive bacteria such as Staphylococcus aureus. For example, Non-Patent Document 1 describes that lysolecithin that is a kind of lysophospholipids is bacteriostatic to and has a bactericidal effect to Staphylococcus aureus. Also, Patent Document 1 describes that lysolecithin inhibits germination of heat-resistant spore-forming bacteria.

Patent Document 1: Japanese Patent Application Laid-open No. 5-11937

Non-Patent Document 1: "Inflammation" (USA), Springer, September, 1979, 3(4), p. 365-377

SUMMARY OF INVENTION

Problem to be Solved by the Invention

However, Non-Patent Document 1 and Patent Document 1 do not describe that lysolecithin has an effect to multidrug resistant bacteria such as MRSA. Thus, knowledge about substances other than antibiotics resistant to and having bacteriostatic effects to multidrug resistant bacteria and their properties are insufficient.

In view of the circumstances as described above, an object of the present invention to provide a multidrug-resistant Gram positive bacteria antibacterial agent containing as an active ingredient a novel component to which multidrug-resistant bacteria are not resistant, and an external agent containing the same.

Means for Solving the Problem

The present inventors have extensively studied to achieve the above-described object. As a result, the present inventors have found that an amphipathic compound having an HLB value of greater than 9.5 and 20 or less and an acyl group is used as an active ingredient of a multidrug resistant Gram-positive bacteria antibacterial agent, thereby exhibiting a high antibacterial activity to multidrug resistant Gram-positive bacteria, and have completed the present invention.

Specifically, the present invention is:

(1) A multidrug resistant Gram-positive bacteria antibacterial agent containing an amphipathic compound having an HLB value of greater than 9.5 and 20 or less and an acyl group as an active ingredient, the amphipathic compound having an acyl group being monoacyl glycerophospholipid and/or sucrose fatty acid ester.

(2) The multidrug resistant Gram-positive bacteria antibacterial agent according to (1),
  in which the monoacyl glycerophospholipid includes lyso phosphatidylcholine.

(3) The multidrug resistant Gram-positive bacteria antibacterial agent according to (2),
  in which the monoacyl glycerophospholipid includes those derived from egg yolk.

(4) The multidrug resistant Gram-positive bacteria antibacterial agent according to any of (1) to (3),
  in which the active ingredient is contained at a concentration of 300 ppm or more.

(5) An external agent containing the multidrug resistant Gram-positive bacteria antibacterial agent according to any of (1) to (4).

By the antibacterial agent containing an amphipathic compound having an HLB value of greater than 9.5 and 20 or less and an acyl group as an active ingredient, the amphipathic compound having an acyl group being monoacyl glycerophospholipid and/or sucrose fatty acid ester, it will be possible to sterilize the multidrug-resistant Gram-positive bacteria. Alternatively, in order to produce the multidrug resistant Gram-positive bacteria antibacterial agent, it will be possible to use the amphipathic compound having an HLB value of greater than 9.5 and 20 or less and an acyl group being monoacyl glycerophospholipid and/or sucrose fatty acid ester.

Effect of the Invention

According to the present invention, it is possible to provide a multidrug-resistant Gram positive bacteria antibacterial agent containing as an active ingredient a novel component to which multidrug-resistant bacteria are not resistant, and an external agent containing the same.

MODES FOR CARRYING OUT THE INVENTION

Hereinafter, the present invention will be described in detail. Herein, "%" means "% by mass" in the present invention. Also the term "antibacterial properties" or "antibacterial activity" in the following description means the properties or its effects for inhibiting widely the growth of bacteria, and also includes bactericidal properties or a bactericidal activity for killing bacteria and inhibiting their growth.

<Feature of the Present Invention>

The multidrug resistant Gram-positive bacteria antibacterial agent according to the present invention features to contain an amphipathic compound having an HLB value of greater than 9.5 and 20 or less and an acyl group as an active ingredient, and the amphipathic compound having an acyl group is monoacyl glycerophospholipid and/or sucrose fatty acid ester. With such a feature, even for multidrug resistant Gram-positive bacteria, it can provide an antibacterial agent having good antibacterial properties.

<Multidrug-Resistant Gram-Positive Bacteria>

Multidrug-resistant Gram-positive bacteria refers to Gram-positive bacteria resistant to multiple drugs, for example, methicillin-resistant *Staphylococcus aureus* (MRSA), vancomycin-resistant *Staphylococcus aureus* (VRSA), Vancomycin-resistant enterococci (VRE), penicillin-resistant *Streptococcus pneumoniae* (PRSP), and the like.

<Gram-Positive Bacteria>

Gram-positive bacteria refer to bacteria that are stained blue or violet by gram staining, and include, for example, *Staphylococcus aureus* and the like. Gram-positive bacteria feature of having a thick peptidoglycan layer around a cell membrane and having no outer membrane on a periphery of the cell membrane. Gram-positive bacteria is not limited to Gram-positive cocci or Gram-positive bacilli.

<HLB Value>

The HLB (Hydrophile-Lipophile Balance) value of the amphipathic compound according to the present invention is greater than 9.5 and 20 or less, greater than 10 and 19 or less, 13 or more and 16 or less. The HLB value is a measure of the balance between hydrophilicity and hydrophobicity of the amphiphilic compound. The greater the HLB value is, the higher the hydrophilicity is. In general, the amphiphilic compound has the following characteristics by their HLB value. Specifically, the compound having an HLB value of about 1 to 6 is not dispersed in water or dispersed only partially. The compound having an HLB value of about 6 to 9.5 is dispersed in water by mixing to form emulsion. The compounds having an HLB value of 10 to 13 is dissolved in water to be, for example, a translucent aqueous solution. The compound having an HLB value of about 13 to 20 is dissolved in water to be, for example, a clear aqueous solution, but is less dissolved in oil. The amphiphilic compound having an HLB value within the above-described range has relatively high hydrophilic and is easily dissolved in water. The antibacterial agent according to the present invention containing such an amphiphilic compound can exhibit an excellent antibacterial activity to multidrug resistant Gram-positive bacteria such as MRSA.

<Method of Calculating HLB Value>

The HLB value of the amphiphilic compound according to the invention may be calculated as follows: Specifically, two types of amphiphilic compounds A and B are mixed to provide an emulsifier. Using the emulsifier, fat or oil is emulsified in water. The HLB value at which emulsification is best performed is regarded as a "required HLB value of the oil or fat". If the required HLB of the oil or fat and the HLB value of the compound A are known, it is possible to determine the HLB value of the compound B from the equation (1) by measuring the masses of compound A and compound B, respectively. In this manner, it is possible to determine the appropriate HLB value not only of the nonionic surfactant, but also of an amphoteric surfactant such as monoacyl glycerophospholipid.

$$(\text{Required HLB}) = (X \times H_A Y \times H_B)/(X+Y) \quad (1)$$

X: Weight of compound A
Y: Weight of compound B
$H_A$: HLB value of compound A
$H_B$: HLB value of compound B <Amphiphilic Compound Having Acyl Group>

The amphiphilic compound having an acyl group according to the present invention acts as the active ingredient of the antibacterial agent according to the present invention. The amphiphilic compound according to the present invention is monoacyl glycerophospholipid and/or sucrose fatty acid ester, and may have one or more acyl groups. The acyl group may have about 16 to 20 carbon atoms, for example.

<Iodine Value of Amphiphilic Compound Having Acyl Group>

An iodine value of the amphiphilic compound having an acyl group is, for example, 25 or less, 20 or less, or 9 or less. The iodine value is provided by converting the amount (g) of halogen that reacts with 100 g of a substance of interest into the amount of iodine. If the iodine value is low, it can be evaluate that the number of double bonds between carbons contained in the fatty acid constituting the acyl group is small, and a percentage of saturated fatty acids is high. Therefore, when the iodine value of the amphiphilic compound is 25 or less, a saturated fatty acid having a more stable chemical structure may effectively approach a bacterial cell surface of multidrug-resistant Gram-positive bacteria, thereby exhibiting an antibacterial effect (see FIG. 2 described later).

<Method of Measuring Iodine Value>

In the present invention, the iodine value can be measured by the Wijs method described below. First, depending on the iodine value of the amphiphilic compound as a sample, a sampling amount shown in Table 1 is weighed accurately. 10 mL of cyclohexane is added to each sample, and is dissolved. Next, 25 mL of iodine monochloride is exactly added thereto. The mixed solution is bottled and shaken lightly. Then, the solution is light-shielded at 20 to 30° C., and is allowed to stand while shaking as appropriate. The time to be left is shown in Table as a reaction time. In addition, 20 mL of a potassium iodide solution and 100 mL of water are added to the solution, which are shaken and mixed. Thereafter, liberated iodine is titrated with 0.1 mol/L of a sodium thiosulfate solution (an indicator is starch reagent, 1 mL). With the similar manner, a blank test is carried out.

TABLE 1

| Iodine value | Sampling amount (g) | Reaction time (min) |
|---|---|---|
| less than 3 | 5 to 3 | 30 |
| 3 to 10 | 3.0 to 2.5 | 30 |
| 10 to 30 | 2.5 to 0.6 | 30 |
| 30 to 50 | 0.6 to 0.4 | 30 |
| 50 to 100 | 0.4 to 0.2 | 30 |
| 100 to 150 | 0.20 to 0.12 | 60 |
| 150 to 200 | 0.15 to 0.10 | 60 |
| 200 or more | 0.12 to 0.10 | 60 |

Then, the iodine value is calculated from the following equation (2)

$$(\text{Iodine value}) = \{(a-b) \times 1.2690\}/(\text{amount of sample (g)}) \quad (2)$$

a: Consumption amount of 0.1 mol/L sodium thiosulfate solution in a blank test (mL)
b: Consumption amount of 0.1 mol/L sodium thiosulfate solution when using a sample (mL)

<Monoacyl Glycerophospholipid>

The amphiphilic compound having an acyl group according to the present invention may include monoacyl glycerophospholipid. By using monoacyl glycerophospholipid having only one acyl group, it is possible to increase hydrophilicity appropriately and to easily satisfy the HLB value within the above-descried range. The acyl group having about 16 to 20 carbon atoms may be used. As the monoacyl glycerophospholipid according to the present invention is an amphoteric surfactant, it is possible to alleviate irritation to skin as compared to an anionic surfactant or a cationic surfactant. Accordingly, when an antibacterial agent containing the above-mentioned monoacyl glycerophospholipid is used as an external agent such as ointments as described later, it is possible to provide a mild external agent. Monoacyl glycerophospholipid may include lysophosphatidyl choline, lysophosphatidyl ethanolamine, lyso phosphatidylinositol, and other lysophospholipids. The lysophospholipid is represented by the following chemical formula 1.

Chemical Formula 1

(where $R_1$ represents an alkyl group, X represents choline, ethanolamine, a hydroxyl group, inositol, and the like.)

<Sucrose Fatty Acid Ester>

The amphiphilic compound having an acyl group according to the present invention may comprise sucrose fatty acid ester. By using the sucrose fatty acid ester having the HLB value of greater than 9.5 and 20 or less, it is possible to exert an antibacterial activity against multidrug resistant Gram-positive bacteria such as MRSA. The sucrose fatty acid ester may include sucrose stearate, sucrose palmitate, sucrose oleate, sucrose laurate, sucrose myristate, and other sucrose fatty acid esters. Moreover, there are from a monoester (1-substituted) where one molecule of fatty acid is bonded in one molecule of sucrose to an octaester (8 substituted) where eight molecules of fatty acid is bonded in one molecule of sucrose. The sucrose fatty acid ester may include any of them. The monoester is represented by the following chemical formula 2.

Chemical Formula 2

(where $R_1$ represents an alkyl group.)

Furthermore, the amphiphilic compound according to the present invention is not especially limited, and may be an ionic surfactant or a non-ionic surfactant. As the ionic surfactant, an amphoteric surfactant may be used, for example. Thus, when the antibacterial agent containing the above-mentioned surfactant is used as an external agent such as ointments as described later, it is possible to alleviate irritation to skin.

<Monoacyl Glycerophospholipid: Lysophospholipid>

Lysophospholipid according to the present invention is provided by hydrolysis with enzyme such as phospholipase A (lysed), extraction and purification. Specifically, the lysophospholipid is glycerophospholipid where a part of the acyl group is liberated by lysis of which is converted into monoacyl glycerophospholipid. The amphiphilic compound may include 90% or more of lysophospholipid in total glycerophospholipid. This makes it possible to increase appropriately the overall hydrophilicity of the amphiphilic compound.

<Monoacyl Glycerophospholipid derived from Food>

The surfactant according to the present invention may include those derived from a food. Thus, it is possible to provide a more safety antibacterial agent. Examples of the surfactant derived from a food include those derived from an egg yolk or soybeans.

<Food-Derived Monoacyl Glycerophospholipid: Monoacyl Glycerophospholipid Derived from Egg Yolk>

As the monoacyl glycerophospholipid from an egg yolk, it is possible to use lysed egg yolk phospholipid. The egg yolk phospholipid is relatively close to phospholipid included in a human cell membrane. Thus, by using the monoacyl glycerophospholipid derived from egg yolk, it is possible to provide an antibacterial agent familiar to skin and a comfortable sense of use. Moreover, as the egg yolk phospholipid generally includes 70% or more of phosphatidylcholine, it is possible to easily extract lysophosphatidylcholine.

<Lysophosphatidylcholine>

The monoacyl glycerophospholipid according to the present invention may include lysophosphatidylcholine. Lysophosphatidylcholine is provided by lysing phosphatidylcholine, and is also referred to as lysolecithin. The lysophosphatidylcholine is represented by the following chemical formula 3.

Chemical Formula 3

(where $R_1$ represents an alkyl group.)

<HLB Value of Lysophosphatidylcholine>

Lyso phosphatidylcholine generally has an HLB value of from 13 or more to 16 or less, which is included within the above-described HLB value. Thus, lysophosphatidylcholine can exert a stable antibacterial activity against multidrug-resistant Gram-positive bacteria such as MRSA.

<Lysophosphatidylcholine Derived from Egg Yolk>

The lysophosphatidyl choline may be derived from egg yolk. Lysophosphatidylcholine derived from egg yolk can be produced by processing an egg yolk solution under the condition that an enzyme such as phospholipase A is activated, extracting with ethanol, and by purifying, for example.

The lysophosphatidylcholine derived from egg yolk has also been approved as a raw material in cosmetics, which is, in particular, familiar to skin and is also used as a moisturizing formulation, etc. Thus, when an external agent containing the antibacterial agent is produced, for example, it is possible to enhance a feeling of use, a moisture retaining property and a therapeutic effect. Furthermore, by using lysophosphatidylcholine derived from egg yolk as a food, it is possible to provide a more comfort and safety antibacterial agent.

<Iodine Value of Lysophosphatidylcholine Derived from Egg Yolk>

Moreover, lysophosphatidylcholine derived from egg yolk may have an iodine value of about 9. Thus, as described above, it is possible to increase the percentage of saturated fatty acids, and can exhibit a stable antibacterial activity. For example, when lysophosphatidylcholine is derived from soybeans, there are much unsaturated fatty acid in the 1-position of a fatty acid that is not liberated by lysis. It is possible to make the iodine value to 25 or less if hydrogenation is carried out, but it is difficult to make the iodine value to 25 or less, if the hydrogenation is not carried out. In contrast, as to lysophosphatidylcholine derived from egg yolk, it is possible to suppress the iodine value low without the hydrogenation, which is also advantageous in manufacturing.

<Antibacterial Agent>

The antibacterial agent according to the present invention may be used as a pharmaceutical additive such as an emulsifier. For example, by adding the antibacterial agent to an MRSA disinfecting ointment, etc., it is possible to enhance the bactericidal effect against MRSA and the like.

It is also possible to add to an anti-inflammatory ointment or the like of skin. The side effect has been found: when a patient uses an agent such as an immunosuppressive agent having an immunosuppression action, a steroid, etc., immunity of a skin surface is lowered, and multidrug-resistant *Staphylococcus aureus* or the like is likely to grow. Therefore, by adding the antibacterial agent according to the present invention to such a patient for anti-inflammatory ointment or the like, it becomes possible to inhibit the growth of multidrug-resistant bacteria.

Alternatively, it is also possible to add to a disinfectant, etc. to a skin lesion site of a decubitus ulcer of an inpatient. It is possible to inhibit the risk of a propagation of multidrug resistant infection that becomes a problem in hospital.

Furthermore, the antibacterial agent according to the present invention can be used for a quasi drug, for example. Specifically, the antibacterial agent can be used as a liquid or spray disinfectant for a human body or an antibacterial constituent of a disinfectant wet sheet, for example. Alternatively, the antibacterial agent can be used as an antibacterial constituent of a disinfectant for a medical device, hospital linen and other articles.

<Content of Active Ingredient>

The antibacterial agent may contain 300 ppm or more, preferably 5000 ppm or more of the amphiphilic compound as the active ingredient. Thus, it is possible to exert a significant antibacterial effect against the multidrug resistant Gram-positive bacteria such as MRSA.

<Possible Combination of Other Antibacterial Agents>

The antibacterial agent according to the present invention can be used in combination with other antibacterial agents. Examples of such other antibacterial agents, for example, include a nitroimidazole antibiotic (e.g., tinidazole and metronidazole), a tetracycline based drug (tetracycline, minocycline, doxycycline), a penicillin-based drug (e.g., amoxicillin, ampicillin, talampicillin, bacampicillin, Renanpishirin, mezlocillin, sultamicillin), a cephalosporin-based drug (e.g., cefaclor, cefadroxil, cephalexin, cefpodoxime proxetil, cefixime, cefdinir, ceftibuten, cefotiam hexetil, cefetamet pivoxil, cefuroxime axetil), a penem-based drug (e.g., Furopenem, lithipenem apoxyl), a macrolide-based drug (e.g., erythromycin, oleandomycin, josamycin, midecamycin, rokitamycin, clarithromycin, roxithromycin, azithromycin), a lincomycin-based agent (e.g., lincomycin, clindamycin), an aminoglycoside-based drug (e.g., paromomycin), a quinolone-based agent (e.g., ofloxacin, levofloxacin, norfloxacin, enoxacin, ciprofloxacin, lomefloxacin, tosufloxacin, fleroxacin, Supafurokisashin, temafloxacin, Najifokisashin, grepafloxacin, Pazufokisashin) as well as nitrofurantoin.

<External Agent>

The antibacterial agent against multidrug-resistant Gram-positive bacteria according to the present invention may be contained in an external agent. Thus, it is possible to provide an external agent having germicidal and antibacterial activity against the multidrug-resistant bacteria such as MRSA. Examples of the external agent according to the present invention include sprays, creams, liquids, gels, lotions and the like other than the following ointments.

The external agent according to the present invention may also contain lysophosphatidylcholine derived from egg yolk as the antibacterial agent. As described above, lysophosphatidylcholine derived from egg yolk has been also approved as a raw material for cosmetics, and may enhance skin moisture retention and a skin barrier function. In this way, it is possible to provide an external agent with an improved feeling of use, and to enhance the therapeutic effect of the external agent.

<Components Incorporated into External Agent>

To the external agent according to the present invention, additives commonly used in a range that does not impair the effects of the present invention other than the above-mentioned antibacterial agent, such as emulsifiers, wetting agents, stabilizers, stabilizing agents, dispersing agents, plasticizers, pH adjusting agents, absorption enhancers, gelling agents, preservatives, fillers, preserving agents, antiseptic agents, dyes, perfumes, fresheners, thickeners, antioxidants, whitening agents, ultraviolet absorbers, bacteriostats, substances with a bacteriostatic effect, and drug components such as immunosuppressive agents and steroids may be blended. Examples of the components include cationic polysaccharides (e.g., cationized hyaluronic acid, cationized hydroxyethyl cellulose, cationized guar gum, cationized starch, cationized locust bean gum, cationized dextran, cationized chitosan, cationized honey, etc.), anionic surfactants (e.g., alkylbenzene sulfonate, polyoxyalkylene alkyl ether sulfate, alkyl sulfate, olefin sulfonates, fatty acid salts, dialkyl sulfosuccinate salts, etc.), nonionic surfactants (e.g., polyoxyethylene fatty acid esters, polyoxyethylene hardened castor oil derivatives, etc.), cationic surfactants (e.g., alkyltrimethylammonium salts, dialkyldimethylammonium salts, alkylpyridinium salts, stearyl trimethyl ammonium chloride, etc.), amphoteric surfactants (e.g., alkyl betaines, alkyl amidopropyl betaines, imidazolinium betaines, egg yolk lecithin, soybean lecithin, etc.), oils (e.g., silicones, silicone derivatives, liquid paraffin, squalane, beeswax, carnauba wax, olive oil, avocado oil, camellia oil, jojoba oil, horse oil, etc.), humectants (e.g., sodium hyaluronate, hyaluronic acid hydrolysis, acetylation hyaluronic acid, hyaluronic acid dimethyl silanol, ceramide, lauroyl disodium phytosteryl octyldodecyl, phytoglycogen, hydrolysis shell membrane, trehalose, glycerin, atelocollagen, sorbitol, maltitol, 1,3-butylene glycol, etc.), higher fatty acids (e.g., lauric acid, behenic acid, palmitic acid, stearic acid, isostearic acid, oleic acid, etc.), higher alcohols (e.g., cetyl alcohol, stearyl alcohol, behenyl alcohol, isostearyl alcohol, batyl alcohol, etc.), polyhydric alcohols (e.g., glycerin, diglycerin, 1,3-propanediol, propylene glycol, polyethylene glycol, pentylene glycol, etc.), thickening agents (e.g., cellulose ethers, carboxyvinyl polymers, xanthan gum, dextrin palmitate, etc.), amphoteric polymer resin compounds (e.g., betaine dialkylaminoalkyl acrylate copolymer, etc.), cationic polymer resin compounds (such as a vinyl pyrrolidone/dimethylaminoethyl methacrylate copolymer cationic compound, a polydimethyl diallyl ammonium halide cationic polymer, etc.), preservatives (e.g., methylparaben, ethylparaben, butylparaben, propylparaben, phenoxyethanol, etc.), antioxidants (e.g., tocopherol phenols, BHT, etc.), metal sequestering agents (such as edetic acid salts, etidronic acid salts, etc.), UV absorbers (e.g., benzophenone derivatives, p-aminobenzoic acid derivatives, methoxy cinnamic acid derivatives, etc.), ultraviolet reflection agents (e.g., oxide titanium, zinc oxide, etc.), protein hydrolyzates (e.g., keratin peptides, collagen peptides, soy peptides, wheat peptides, milk peptides, silk peptides, egg white peptides, etc.), bacteriostatic agents (e.g., lysozyme, glycine, sodium acetate, ε-polylysine), drugs such as immunosuppressive agents and steroids (e.g., tacrolimus, cyclosporine, clobetasol propionate, acetic acid diflorasone, difluprednate, betamethasone dipropionate, valerate diflucortolone, Fureoshinonido, amcinonide, betamethasone butyrate propionate, valerate dexamethasone, fradiomycin sulfate, fluocinolone acetonide, alclometasone propionate, hydrocortisone, Crotamine etc.), amino acids (e.g., arginine, glutamic acid, glycine, alanine, hydroxyproline, cysteine, serine, L-theanine, etc.), natural product extracts (Kujin extract, Kajiru extract, Tenchika extract, seaweed extract, eucalyptus extract, royal jelly extract, rosemary extract, beech extract, etc.), other functional ingredients (coenzyme Q10, arbutin, polyquaternium 51, elastin, platinum nano colloid, retinol palmitate, panthenol, allantoin, lysine sodium dilauroyl glutamic acid, magnesium ascorbyl phosphate, L-ascorbic acid 2-glucoside, ellagic acid, kojic acid, linoleic acid, tranexamic acid, etc.), phospholipid polymers, perfumes, and dyes.

<External Agent: Ointment>

The external agent according to the present invention may be an ointment. The ointment containing the antibacterial agent according to the present invention may, for example, be produced by melting the antibacterial agent to a base, and then kneading them. The antibacterial agent according to the present invention has an emulsifying effect, and therefore can be well mixed with a variety of bases. The amount of the antibacterial agent in the ointment is not especially limited. The following ingredients may be added to the ointment as an additive.

<Ingredients Added to Ointment>

The base of the ointments may include any one or a mixture of two or more of higher fatty acids and esters thereof (adipic acid, myristic acid, palmitic acid, stearic acid, oleic acid, adipic acid ester, myristic acid ester, palmitic acid ester, diethyl sebacate, hexyl laurate, iso-octane cetyl, lanolin and lanolin derivatives, etc.), waxes (whale wax, beeswax, ceresin, etc.), higher alcohols (cetanol, stearyl alcohol, cetostearyl alcohol, etc.), hydrocarbons (hydrophilic vaseline, white petrolatum, purified lanolin, liquidity paraffin, etc.) and animal or vegetable oils. If desired, in addition to the base of the ointment, paraffins such as liquid paraffin, lanolin, animal and vegetable oils, natural wax, hydrogenated soybean phospholipids (lecithin) or a higher alcohol may be included. The ointment base included in the ointment according to the present invention may be miscible or immiscible with a solubilizer.

Next, the present invention will be further described based on examples, etc.

EMBODIMENTS

Example 1

Firstly, an antibacterial agent in Example 1 was prepared. In Example 1, as the amphiphilic compound, which is the active ingredient of the antibacterial agent, lyso phosphatidylcholine derived from egg yolk (manufactured by Kewpie Corporation, egg yolk lysolecithin LPC-1) was used. The lyso phosphatidylcholine in Example 1 had the HLB value of 14 and the iodine value of 9. Table 2 shows substance names, derived sources, and HLB values in Examples and Comparative Examples, respectively.

TABLE 2

| | Ingredient of antibacterial agent | Derived from | HLB value |
|---|---|---|---|
| Ex. 1 | lyso phosphatidylcholine | egg yolk | 14 |
| Ex. 2 | lysophospholipids | soybeans | 11 to 20 |
| Ex. 3 | sucrose fatty acid ester | synthesized | 15 |
| Ex. 4 | sucrose fatty acid ester | synthesized | 19 |
| Comp. Ex. 1 | lyso phosphatidyl glycerol | soybeans | 22 |
| Comp. Ex. 2 | sucrose fatty acid ester | synthesized | 1 |
| Comp. Ex. 3 | glycerin fatty acid ester | synthesized | 4.3 |
| Comp. Ex. 4 | sucrose fatty acid ester | synthesized | 6 |
| Comp. Ex. 5 | glycerin fatty acid ester | synthesized | 7 |
| Comp. Ex. 6 | sucrose fatty acid ester | synthesized | 9.5 |

Next, a predetermined amount of lyso phosphatidylcholine was weighed, which was agitated and dissolved into sterile purified water (hereinafter referred to as purified water). As a result, 20 mL of a test solution containing 0.5 mass % (5000 μg/mL, 5000 ppm) of lyso phosphatidylcholine was purified.

Subsequently, the test solution was two-fold diluted in three stages using purified water. As a result, the test solution having a concentration of 5000 ppm (5000 μg/mL), 1250 ppm (1250 μg/mL), or 313 ppm (313 μg/mL) was prepared.

Example 2

In Example 2, as the amphiphilic compound, hydrogenated soybean lysophospholipid (manufactured by Nikko Chemicals Co., Lecinol LL-20) was used. It is conceivable that a plurality of phospholipids may be mixed to provide the soybean lysophospholipid in Example 2, and it confirms that the soybean lysophospholipid had an HLB value of 11 to 20. The iodine value was 20 or less. The soybean lysophospholipid is represented by the above formula 1. The soybean lysophospholipid was prepared in the same manner as in Example 1, and the test solution having a concentration of 5000 ppm (5000 μg/mL), 1250 ppm (1250 μg/mL), or 313 ppm (313 μg/mL) was prepared. When the soybean lysophospholipid was not easily dissolved in purified water, it was heated to about 70° C.

Comparative Example 1

In Comparative Example 1, as the amphiphilic compound, soybean lyso phosphatidyl glycerol (manufactured by Nagase ChemteX, lyso PG Nagase) was used (see Table 2). The lyso phosphatidyl glycerol in Comparative Example 1 had the HLB value of about 22. The lysophosphatidyl glycerol is represented by the following chemical formula 4.

Chemical formula 4

(where $R_1$ represents an alkyl group.)

The lyso phosphatidyl glycerol was prepared in the same manner as in Example 1, and the test solution having a concentration of 5000 ppm (5000 μg/mL), 1250 ppm (1250 μg/mL), or 313 ppm (313 μg/mL) was prepared. When the lyso phosphatidyl glycerol was not easily dissolved in purified water, it was heated to about 70° C.

<Test Example 1>

Examples 1, 2, and Comparative Example 1 were used to determine the antibacterial properties.

(Test Bacteria Strain)

Firstly, the strain 1 and strain 2 shown in Table 3 were cultured at 35° C. for 48 hours in each standard agar medium (SPC (Standard Plate Count)). Then, the resulting strains were suspended in physiological saline to have the number of about $10^7$ cfu/mL.

TABLE 3

| | Strain |
|---|---|
| Strain 1 | Staphylococcus aureus |
| Strain 2 | methicillin-resistant Staphylococcus aureus |

(Preparation of Test Solution)

Compounds in Example 1, Comparative Example 1, and Example 2 were prepared as described above, and the test solution having each concentration was prepared.

(Determination of Antibacterial Properties by a Disk Method)

Firstly, 20 mL of a liquid standard agar medium and 1 mL of each test bacteria strain were added to a sterile Petri dish and mixed. Then, the Petri dish was cooled to solidify the culture medium. The culture medium solidified was further dried for about 20 to 30 minutes in a clean bench.

Next, a sterile paper disk was placed on the culture medium with sterile tweezers and was adhered by pressing. Then, 50 μL of each test solution prepared in Example 1, Example 2 and Comparative Example 1 was dropped onto a predetermined disk, and was allowed to stand until the test liquid was absorbed on the disk. Furthermore, the culture medium was cultured for about 48 hours at 30° C.

After the culture, a diameter of the part (inhibition circle) where no bacteria was grown around the paper disk was measured with a measure.

Figure 1:
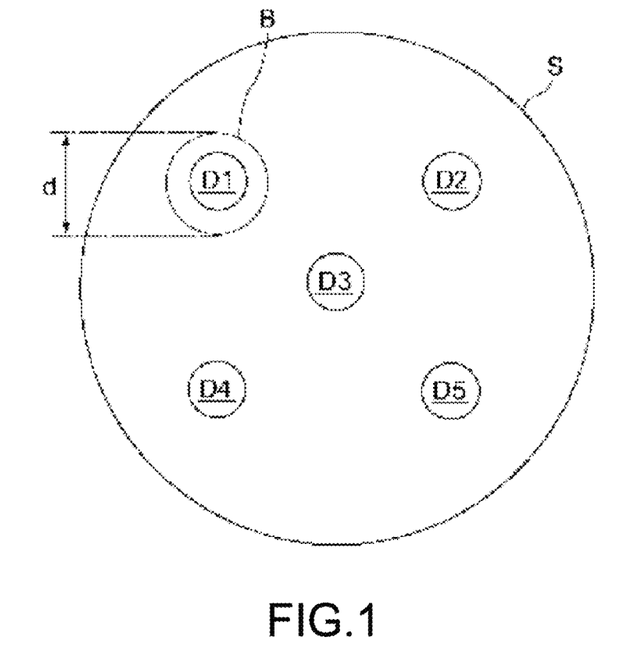
FIG. 1 A schematic diagram for the explanation of a disk method.

FIG. 1 is a schematic diagram for the explanation of the disk method, where symbol S represents the petri dish, symbols D1 to D5 represent the paper disks, a symbol B represents the inhibition circle. The test liquid having high antibacterial properties is exuded from the paper disk and sterilizes bacteria contained in the culture medium. In this way, the inhibition circle is formed. The higher the antibacterial properties are, the greater the inhibition circle becomes. Conversely, if the antibacterial properties are low, the bacteria is not sufficiently sterilized, and no inhibition circle is formed. Therefore, by measuring the diameter d of the inhibition circle, the antibacterial properties are evaluated.

(Result)

Table 4 shows the results of Test Example 1. As shown in Table 4, in each test solution in Example 1, the inhibition circle having a diameter of greater than 10 mm was observed with respect to Staphylococcus aureus and MRSA. Thus, it was confirmed that the lyso phosphatidylcholine derived from egg yolk in Example 1 exerted the antibacterial effect against MRSA. Moreover, in Example 1, the inhibition circle greater than 10 mm was also observed against MRSA for the test solution having a concentration of 313 ppm. Thus, the lyso phosphatidylcholine derived from egg yolk in Example 1 was confirmed to have sufficient antibacterial properties at a concentration of 300 ppm or more.

TABLE 4

| | | Strain | | | | | |
|---|---|---|---|---|---|---|---|
| | | Strain 1 (Staphylococcus aureus) Test solution concentration (ppm) | | | Strain 2 (methicillin-resistant Staphylococcus aureus) Test solution concentration (ppm) | | |
| Test solution | HLB value | 5000 | 1250 | 313 | 5000 | 1250 | 313 |
| Ex. 1 | 14 | 18.0 | 15.0 | 12.5 | 19.0 | 16.0 | 15.0 |
| Ex. 2 | 11 to 20 | 12.0 | 12.0 | 0.0 | 13.0 | 0.0 | 0.0 |
| Comp. Ex. 1 | 22 | 9.0 | 0.0 | 0.0 | 10.0 | 0.0 | 0.0 |

Diameter of Inhibition Circle: mm

In Example 2, the inhibition circle having a diameter of 13.0 mm was formed in the test solution having a concentration of 5000 ppm against MRSA, and the inhibition circle having a diameter of 12.0 mm was formed in the test solution having a concentration of 1250 ppm against Staphylococcus aureus was formed. The antibacterial properties in Example 2 are lower than those in Example 1. This result is conceivable that a degree of purification of the hydrogenated soybean lysophospholipid in Example 2 may be involved.

On the other hand, in Comparative Example 1, although the inhibition circle having a diameter of 10.0 mm was formed in the concentration of 5000 ppm against MRSA and Staphylococcus aureus, no inhibition circle was formed in the concentration of 1250 ppm or 313 ppm against MRSA and Staphylococcus aureus. Thus, even in the amphiphilic compound having an acyl group, when the HLB value is greater than 20, it is conceivable that it has not sufficient antibacterial properties against MRSA.

Next, in order to evaluate the antibacterial properties by the value of the HLB value, Examples 3 to 4 and Comparative Examples 2 to 6 were prepared.

Example 3

In Example 3, as the amphiphilic compound, sucrose fatty acid ester (manufactured by Dai-ichi Kogyo Seiyaku Co., Ltd., DK ester F-160) was used (see Table 2). The sucrose fatty acid ester in Example 3 had the HLB value of 15. The sucrose fatty acid ester was prepared in the same manner as in Example 1, and the test solution having a concentration of 5000 ppm (5000 µg/mL), 1250 ppm (1250 µg/mL), or 313 ppm (313 µg/mL) was prepared. When the sucrose fatty acid ester was not easily dissolved in purified water, it was heated to about 70° C.

Example 4

In Example 4, as the amphiphilic compound, sucrose fatty acid ester (manufactured by Dai-ichi Kogyo Seiyaku Co., Ltd., DK ester SS) was used (see Table 2). The sucrose fatty acid ester in Example 3 had the HLB value of 19. The antibacterial agent was prepared using the sucrose fatty acid ester in the same manner as in Example 1, and the test solution having a concentration of 5000 ppm (5000 µg/mL), 1250 ppm (1250 µg/mL), or 313 ppm (313 µg/mL) was prepared. When the sucrose fatty acid ester was not easily dissolved in purified water, it was heated to about 70° C.

Comparative Example 2

In Comparative Example 2, as the amphiphilic compound, sucrose fatty acid ester (manufactured by Dai-ichi Kogyo Seiyaku Co., Ltd., DK ester F-10) were used (see Table 2). The sucrose fatty acid ester in Comparative Example 2 had the HLB value of 1.

As the sucrose fatty acid ester in Comparative Example 2 was not dissolved in purified water, it was prepared using Japanese Pharmacopoeia soybean oil (manufactured by Kaneda Co., Ltd.) (hereinafter referred to as soybean oil). That is to say, the sucrose fatty acid ester was diluted stepwise similar to Example 1 except that purified water was not used, but the soybean oil was used, and the test solution having a concentration of 5000 ppm (5000 µg/mL), 1250 ppm (1250 µg/mL), or 313 ppm (313 µg/mL) was prepared.

Comparative Example 3

In Comparative Example 3, as amphipathic compounds, glycerin fatty acid ester (manufactured by Riken Vitamin Co., EMALGEE MS flour) was used (see Table 2). The glycerin fatty acid ester had the HLB value of 4.3. The glycerin fatty acid ester was prepared using the soybean oil in the same manner as in Comparative Example 2, and the test solution having a concentration of 5000 ppm (5000 µg/mL), 1250 ppm (1250 µg/mL), or 313 ppm (313 µg/mL) was prepared.

Comparative Example 4

In Comparative Example 4, as the amphiphilic compound, sucrose fatty acid ester (manufactured by Dai-ichi Kogyo Seiyaku Co., Ltd., DK ester F-50) was used (see Table 2). The sucrose fatty acid ester in Comparative Example 4 had the HLB value of 6. The sucrose fatty acid ester was prepared in the same manner as in Example 1, and the test solution having a concentration of 5000 ppm (5000 µg/mL), 1250 ppm (1250 µg/mL), or 313 ppm (313 µg/mL) was prepared. When the sucrose fatty acid ester was not easily dissolved in purified water, it was heated to about 70° C.

Comparative Example 5

In Comparative Example 5, the amphiphilic compound, glycerin fatty acid ester (manufactured by Riken Vitamin Co., Ltd., POEM M-100) was used (see Table 2). The glycerin fatty acid ester in Comparative Example 5 had the HLB value of 7. The glycerin fatty acid ester was prepared in the same manner as in Example 1, and the test solution having a concentration of 5000 ppm (5000 µg/mL), 1250 ppm (1250 µg/mL), or 313 ppm (313 µg/mL) was prepared. When the glycerin fatty acid ester was not easily dissolved in purified water, it was heated to about 70° C.

Comparative Example 6

In Comparative Example 6, as the amphiphilic compound, sucrose fatty acid ester (manufactured by Dai-ichi Kogyo Seiyaku Co., Ltd., DK ester F-90) was used (see Table 2). The sucrose fatty acid ester in Comparative Example 9.5 had the HLB value of 7. The sucrose fatty acid ester was prepared in the same manner as in Example 1, and the test solution having a concentration of 5000 ppm (5000 µg/mL), 1250 ppm (1250 µg/mL), or 313 ppm (313 µg/mL) was prepared. When the sucrose fatty acid ester was not easily dissolved in purified water, it was heated to about 70° C.

<Test Example 2>

Examples 1, 3, 4 and Comparative Examples 2 to 6 were used to determine the antibacterial properties of the test bacteria strains shown in Table 3 using the disk method similar to Test Example 1. This procedure is the same as in Test Example 1, the description thereof is omitted.

(Result)

Table 5 shows the results of Test Example 2. As shown in Table 5, in each test solution in Comparative Examples 2 to 5 each having the HLB value of 1 to 7, no inhibition circle was formed with respect to MRSA and *Staphylococcus aureus*. In Comparative Example 6 having the HLB value of 9.5, the inhibition circle having a diameter of 14 mm was formed with respect to MRSA at a concentration of 5000 ppm, but no inhibition circle was formed with respect to MRSA at a concentration of 1250 ppm and 313 ppm. It is thus conceivable that the amphipathic compound having an acyl group but having the HLB value of 9.5 or less has no sufficient antibacterial properties against MRSA. On the other hand, it was confirmed that in each test solution in Examples 1 to 4, the inhibition circle having a diameter of greater than 10 mm was observed with respect to *Staphylococcus aureus* and MRSA.

TABLE 5

| Test solution | HLB value | Strain 1 (*Staphylococcus aureus*) Test solution concentration (ppm) | | | Strain 2 (MRSA) Test solution concentration (ppm) | | |
|---|---|---|---|---|---|---|---|
| | | 5000 | 1250 | 313 | 5000 | 1250 | 313 |
| Ex. 1 | 14 | 18 | 17 | 15 | 18 | 16 | 14 |
| Ex. 3 | 15 | 16 | 16 | 14 | 16 | 15 | 14 |
| Ex. 4 | 19 | 20 | 18 | 17 | 18 | 17 | 15 |
| Comp. Ex. 2 | 1 | 0 | 0 | 0 | 0 | 0 | 0 |
| Comp. Ex. 3 | 4.3 | 0 | 0 | 0 | 0 | 0 | 0 |
| Comp. Ex. 4 | 6 | 0 | 0 | 0 | 0 | 0 | 0 |
| Comp. Ex. 5 | 7 | 0 | 0 | 0 | 0 | 0 | 0 |
| Comp. Ex. 6 | 9.5 | 0 | 0 | 0 | 14 | 0 | 0 |

<Result of Test Example 1 and Test Example 2 (Summary)>

From the results of Test Examples 1 and 2, it was confirmed that the amphipatic compound having an acyl group and the HLB value of greater than 9.5 has sufficient antibacterial properties. In particular, in the test solution of Example 1 containing lyso phosphatidylcholine derived from egg yolk, sufficient antibacterial properties were confirmed even at a concentration of 300 ppm or more. On the other hand, if the HLB value was 1 to 7, it was confirmed that the amphiphilic compound even having an acyl group had no antibacterial properties against MRSA. In addition, the result of Comparative Example 1 in Test Example 1, if the HLB value was greater than 20, it has been suggested that the antibacterial properties could not be exerted. Therefore, it can be said that the amphipathic compound having an acyl group and an HLB value of greater than 9.5 to 20 or less has antibacterial properties against MRSA.

From the above results, it was confirmed that the antibacterial properties against MRSA of the amphiphilic compound were greatly concerned with a balance between hydrophilicity and hydrophobicity and there existed the range of optimal HLB value. It will be discussed below in the light of these results.

<Discussion>

Figure 2:
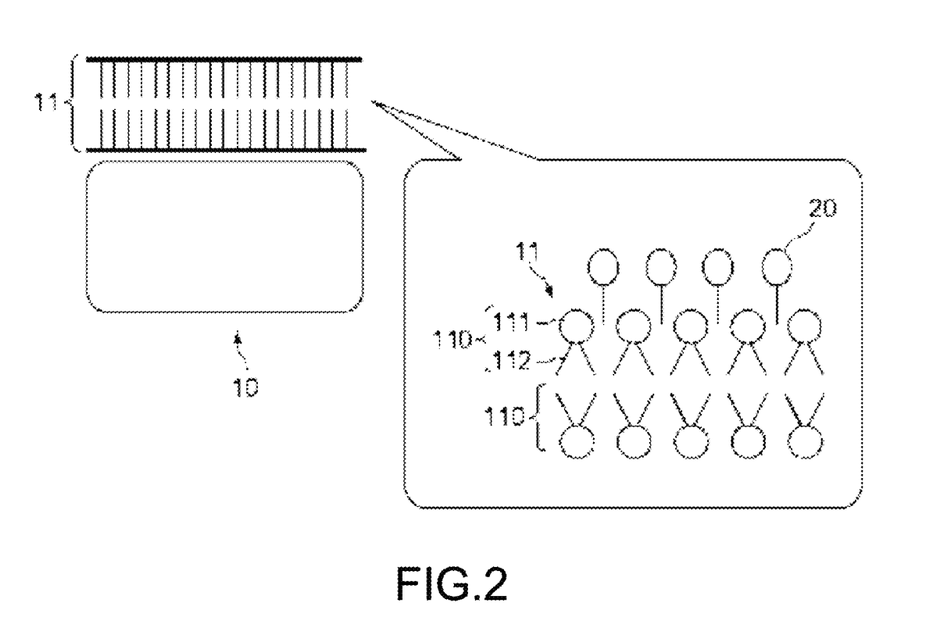
FIG. 2 A schematic diagram for the explanation of an envisaged mechanism of the antibacterial agent according to the present invention.

FIG. 2 is a diagram for the explanation of an envisaged mechanism of the antibacterial agent according to the present invention. As shown in FIG. 2, the multidrug resistant Gram-positive bacteria 10 are covered with the cell membrane 11, and includes cytoplasm or the like therein. The cell membrane 11 has a lipid biolayer mainly including fatty acid 110 having a hydrophilic group 111 and a hydrophobic group1 112, as shown in an enlarged view in FIG. 2.

For a purpose of explanation, only a part of the cell membrane 11 is shown in FIG. 2.

The amphiphilic compound 20 having the HLB value of greater than 9.5 and less than 20 has appropriate hydrophilicity with the fatty acid 110 of the cell membrane 11 by the balance between hydrophilicity and hydrophobicity. The amphiphilic compound 20 can utilize the hydrophilicity to interrupt as a wedge into the lipid bilayer of the cell membrane 11. As a result, the structure of the cell membrane 11 is disordered, permeability is increased, and the cytoplasmic components leak out. It is conceived that the amphiphilic compound 20 thereby kills the multidrug resistant Gram-positive bacteria 10.

In particular, Gram-positive bacteria has a feature having no outer membrane as compared to Gram-negative bacteria. Thus, the amphiphilic compound 20 approaches more effectively to the cell membrane 110, and exerts the antibacterial activity.

Furthermore, it is conceived that multidrug-resistant Gram-positive bacteria hardly acquires drug resistance to the antibacterial agent according to the present invention unlike the known antibiotics. For example, a β-lactam agent such as penicillin and methicillin is an antibiotic, binds to a PBP (Penicillin-binding Protein) that is a bacterial cell wall synthesizing enzyme, inhibits the completion of the network structure of the cell wall, and lyses the bacteria, thereby exerting the antibacterial activity. In contrast, multidrug resistant Gram-positive bacteria generates β-lactamase that dissolves penicillin, thereby acquiring drug resistance to penicillin. Although methicillin is not decomposed by β-lactamase, a cell wall synthesizing enzyme PBP2a that is low affinity with the β-lactam agent is expressed. Thus, multidrug resistant Gram-positive bacteria has acquired resistance to drugs by mainly expressing a new biochemical mechanism such as decomposing the drug itself or lowering affinity with the drug.

Meanwhile, in the amphiphilic compound according to the present invention, by physically destroying the cell membrane, the antibacterial activity is exerted, as described above. That is to say, as the antibacterial agent according to the present invention has an antibacterial mechanism that is different from the antibiotics. It is therefore conceivable that it is difficult to acquire resistance by multidrug resistant Gram-positive bacteria such as MRSA. Therefore, it can be said that the antibacterial agent according to the present invention reduces the risk of drug resistance and is widely used with high reliability.

Furthermore, by using the antibacterial agent in Example 1, external agents having the following formulations 1 to 3 were produced, and a feeling of use was examined.

Formulation Example 1: Ointment

In formulation example 1, an ointment having a content including the following formulations was produced using the antibacterial agent in Example 1.

| | (Mixing ratio) |
|---|---|
| Antibacterial agent in Example 1 | 0.5% |
| White petrolatum | 25.0% |
| Stearyl alcohol | 20.0% |
| Propylene glycol | 12.0% |
| Polyoxyethylene hydrogenated castor oil 60 | 4.0% |
| Glycerin monostearate | 1.0% |
| Methyl parahydroxybenzoate | 0.1% |
| Propyl parahydroxybenzoate | 0.1% |
| Purified water | Balance |
| Total | 100% |

Formulation Example 2: Antibacterial Spray

In formulation example 2, an antibacterial spray solution having a content including the following formulation was produced using the antibacterial agent in Example 1. Furthermore, the antibacterial spray solution is filled into commercially available 50 mL volume pump spray container to produce an antibacterial spray for hand disinfection.

| | (Mixing ratio) |
|---|---|
| Antibacterial agent in Example 1 | 0.05% |
| Glycerin | 0.50% |
| Monoglycerides capric acid | 0.20% |
| Ethanol | 50.00% |
| Purified water | Balance |
| Total | 100% |

Formulation Example 3: Antibacterial Cream

In formulation example 3, cream having contents including following formulation was produced using the antibacterial agent in Example 1. Furthermore, 50 g of the cream is filled in a plastic container with a screw cap to prepare antibacterial cream.

| | (Mixing ratio) |
|---|---|
| Antibacterial agent in Example 1 | 0.05% |
| Polyethylene glycol | 4.00% |
| 1,3-propanediol | 6.00% |
| Squalane | 11.00% |
| Dimethicone | 1.00% |
| Cetyl alcohol | 6.00% |
| Stearic acid | 2.00% |

-continued

| (Mixing ratio) | |
|---|---|
| Hydrogenated coco-glycerides | 4.00% |
| Tricaprylin | 8.00% |
| Glycerin monostearate | 3.00% |
| POE (20) cetyl alcohol ether | 2.00% |
| Coenzyme Q10 | 0.03% |
| Ceramide | 0.10% |
| Dilauroyl glutamic acid lysine sodium | 0.10% |
| EDTA-2 sodium | 0.02% |
| Propyl paraben | 0.10% |
| Methylparaben | 0.15% |
| Perfume | Proper |
| Purified water | Balance |
| total | 100% |

When each external agent in the formulation examples 1 to 3 was applied or sprayed to/on skin, a feeling of use was such that the external agent was moist and familiar to the skin. It may be caused that each external agent in the formulation examples 1 to 3 includes the antibacterial agent containing lyso phosphatidylcholine derived from egg yolk in Example 1. Accordingly, the external agent including the antibacterial agent according to the present invention can exert a high antibacterial activity against multidrug resistant Gram-positive bacteria, and enhance skin moisture retention. Also, it is expected to enhance a skin barrier function and a therapeutic effect against multidrug resistant Gram positive bacterial infections by the ointment or the cream.

DESCRIPTION OF SYMBOLS

S petri dish
D1, D2, D3, D4, D5 paper disk
B inhibition circle
10 multidrug-resistant Gram-positive bacteria
11 cell membrane
20 amphiphilic compound
110 fatty acid
111 hydrophilic group
112 hydrophobic group

What is claimed is:

1. A method for treatment of an infection with multidrug resistant Gram-positive bacteria, the method comprising:
    treating the infection by administering to a patient in need thereof a formulation comprising an amphipathic compound having a Hydrophile-Lipophile Balance (HLB) value of equal to or greater than 14 and no more than 20 and an acyl group as an active ingredient, the amphipathic compound being monoacyl glycerophospholipid and/or sucrose fatty acid ester,
    wherein the method comprises administering an effective amount of the formulation exerting an antibacterial action against the multidrug resistant Gram-positive bacteria.
2. The method according to claim 1, further comprising, before treating the infection by administering the amphipathic compound, preparing the amphipathic compound,
    wherein preparing the amphipathic compound comprises heating the amphipathic compound to a temperature of 70° C.
3. The method according to claim 2,
    wherein the active ingredient is present in the formulation at a concentration of 300 ppm or more.
4. The method according to claim 3,
    wherein administering the amphipathic compound comprises applying the amphipathic compound to skin of the patient.
5. The method according to claim 1, wherein the amphipathic compound is monoacyl glycerophospholipid, which includes lysophosphatidylcholine,
    wherein the method further comprises, before treating the infection by administering the amphipathic compound, preparing the amphipathic compound,
    wherein preparing the amphipathic compound comprises extracting the lysophosphatidylcholine from soybean and performing hydrogenation on the lysophosphatidylcholine.
6. The method according to claim 5, wherein preparing the amphipathic compound further comprises measuring an iodine value of the lysophosphatidylcholine.
7. The method according to claim 5,
    wherein the active ingredient is present in the formulation at a concentration of 300 ppm or more.
8. The method according to claim 7,
    wherein administering the amphipathic compound comprises applying the amphipathic compound to skin of the patient.
9. The method according to claim 1, wherein the amphipathic compound is monoacyl glycerophospholipid, which includes lysophosphatidylcholine,
    wherein the method further comprises, before treating the infection by administering the amphipathic compound, preparing the amphipathic compound,
    wherein preparing the amphipathic compound comprises extracting the lysophosphatidylcholine from egg yolk without hydrogenation.
10. The method according to claim 9,
    wherein the active ingredient is present in the formulation at a concentration of 300 ppm or more.
11. The method according to claim 10,
    wherein administering the amphipathic compound comprises applying the amphipathic compound to skin of the patient.
12. The method according to claim 1,
    wherein the amphipathic compound is monoacyl glycerophospholipid, which includes lysophosphatidylcholine.
13. The method according to claim 12,
    wherein the monoacyl glycerophospholipid is derived from egg yolk.
14. The method according to claim 13,
    wherein the active ingredient is present in the formulation at a concentration of 300 ppm or more.
15. The method according to claim 13,
    wherein administering the amphipathic compound comprises applying the amphipathic compound to skin of the patient.
16. The method according to claim 12,
    wherein the active ingredient is present in the formulation at a concentration of 300 ppm or more.
17. The method according to claim 12,
    wherein administering the amphipathic compound comprises applying the amphipathic compound to skin of the patient.
18. The method according to claim 1,
    wherein the amphipathic compound is administered to the patient at a concentration of 300 ppm or more.
19. The method according to claim 18,
    wherein administering the amphipathic compound comprises applying the amphipathic compound to skin of the patient.

20. The method according to claim 1,
wherein administering the amphipathic compound comprises applying the amphipathic compound to skin of the patient.

* * * * *